US00PP12887P2

(12) United States Plant Patent
Bergman

(10) Patent No.: US PP12,887 P2
(45) Date of Patent: Aug. 27, 2002

(54) HIBISCUS PLANT NAMED 'COOL WIND'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 32 days.

(21) Appl. No.: 09/887,107

(22) Filed: Jun. 25, 2001

(51) Int. Cl.[7] ..... A01H 5/00

(52) U.S. Cl. ..... Plt./257

(58) Field of Search ..... Plt./257

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hibiscus plant named 'Cool Wind', characterized by its compact, upright, outwardly spreading, uniform, dense and symmetrical plant habit that is appropriate for container production; glossy dark green leaves; uniform and freely flowering habit; large white-colored flowers with pink-colored throat and short peduncles; good resistance to flower bud abscission; and relative resistance to pathogens common to Hibiscus grown under Florida production conditions.

2 Drawing Sheets

BACKGROUND OF THE INVENTION

The present invention relates to a new and distinct cultivar of Hibiscus, botanically known as *Hibiscus rosa-sinensis*, and hereinafter referred to by the name 'Cool Wind'.

The new Hibiscus is a product of a planned breeding program conducted by the Inventor in Alva, Fla. The objective of the breeding program is to create new freely-branching Hibiscus cultivars with uniform and compact plant habit appropriate for container production, early and uniform flowering, numerous flowers per lateral branch, desirable flower color, and good postproduction longevity.

The new Hibiscus originated from a cross made by the Inventor in Alva, Fla. in early 1996, of a proprietary *Hibiscus rosa-sinensis* selection, designated as code number YB-1388, not patented, as the female, or seed, parent with a proprietary *Hibiscus rosa-sinensis* selection, designated as code number YB-1507, not patented, as the male, or pollen, parent. The cultivar Cool Wind was discovered and selected by the Inventor as a flowering plant within the progeny of the stated cross in a controlled environment in Alva, Fla., on Sep. 4, 1997.

Asexual reproduction of the new Hibiscus by vegetative terminal cuttings taken in a controlled environment in Alva, Fla. since November, 1997, has shown that the unique features of this new Hibiscus are stable and reproduced true to type in successive generations.

SUMMARY OF THE INVENTION

The cultivar Cool Wind has not been observed under all possible environmental conditions. The phenotype may vary somewhat with variations in environment and cultural practices such as temperature, light intensity, water status and/or fertilizer rate or type without, however, any variance in genotype.

The following traits have been repeatedly observed and are determined to be the unique characteristics of 'Cool Wind'. These characteristics in combination distinguish 'Cool Wind' as a new and distinct cultivar:

1. Compact, upright, outwardly spreading, uniform, dense and symmetrical plant habit that is appropriate for container production.
2. Glossy dark green leaves.
3. Uniform and freely flowering habit.
4. Large white-colored flowers with pink-colored throat and short peduncles.
5. Good resistance to flower bud abscission during shipping.
6. Relatively resistant to pathogens common to Hibiscus grown under Florida production conditions.

Compared to plants of the yellow-flowered female parent, the proprietary Hibiscus selection code number YB-1388, plants of the new Hibiscus have darker green foliage, larger flowers and differ in flower color. Compared to plants of the male parent, the proprietary Hibiscus selection code number YB-1507, plants of the new Hibiscus have a more uniform plant habit and smaller flowers.

Plants of the new Hibiscus can be compared to plants of the white-flowered Hibiscus cultivar Coconut Wind, disclosed in U.S. Plant Pat. No. 11,761. In side-by-side comparisons conducted in Alva, Fla., plants of the new Hibiscus differ from plants of the cultivar Coconut Wind in the following characteristics:

1. Plants of the new Hibiscus have darker green foliage than plants of the cultivar Coconut Wind.
2. Plants of the new Hibiscus have white flowers with pink throats whereas plants of the cultivar Coconut Wind have white flowers with red throats.
3. Flowers of plants of the new Hibiscus have more substance and do not bruise as easily as flowers of plants of the cultivar Coconut Wind.
4. Plants of the new Hibiscus are less susceptible to diseases common to Hibiscus grown under Florida production conditions than plants of the cultivar Coconut Wind.

BRIEF DESCRIPTION OF THE PHOTOGRAPHS

The accompanying colored photographs illustrate the overall appearance of the new Hibiscus, showing the colors as true as it is reasonably possible to obtain in colored reproductions of this type. Colors in the photographs may differ slightly from the color values cited in the detailed botanical description which accurately describe the colors of the new Hibiscus.

The photograph on the first sheet comprises a side perspective view of a typical flowering plant of 'Cool Wind'.

The photograph on the second sheet comprises a close-up view of typical flowers and leaves of 'Cool Wind'.

DETAILED BOTANICAL DESCRIPTION

The photographs and following observations, measurements and values describe plants grown in Alva, Fla., with five plants per 15-cm container in polyethylene-covered greenhouses during the winter and spring under conditions which closely approximate commercial production. During the production of the plants, day temperatures ranged from 13 to 37° C. and night temperatures ranged from 13 and 26° C. Plants were about 7 months old when the photographs and the description were taken. In the description, color references are made to The Royal Horticultural Society Colour Chart except where general terms of ordinary dictionary significance are used.

Botanical classification: *Hibiscus rosa-sinensis* cultivar Cool Wind.

Parentage:

*Female or seed parent.*—Proprietary selection of *Hibiscus rosa-sinensis* designated as code number YB-1388, not patented.

*Male or pollen parent.*—Proprietary selection of *Hibiscus rosa-sinensis* designated as code number YB-1507, not patented.

Propagation:

*Type.*—By vegetative terminal cuttings.

*Time to initiate roots.*—About 10 days at temperatures of 24° C.

*Time to develop roots.*—About 28 days at temperatures of 24° C.

*Root description.*—Thick, fibrous and white in color.

Plant description:

*Plant form and growth habit.*—Perennial, evergreen, upright, outwardly spreading, compact, uniform, dense and symmetrical plant habit. Vigorous growth habit.

*Branching habit.*—Freely branching, usually about three to four lateral branches develop after removal of terminal apex.

*Plant height.*—About 25 cm.

*Plant diameter* (*area of spread*).—About 51 cm.

*Lateral branch description.*—Length: About 21 cm. Diameter: About 5.5 mm. Texture: Immature, smooth; mature, woody and rough. Color: Immature: 146A overlain with dark brown, between 187A and 202A. Mature: More brown than 187A.

*Foliage description.*—Arrangement: Alternate, single; numerous; symmetrical. Length: About 9.5 cm. Width: About 7.6 cm. Shape: Ovate. Apex: Acuminate to narrowly acute. Base: Attenuate to obtuse. Margin: Serrate to crenate. Aspect: Undulate, Concave. Texture, upper and lower surfaces: Glabrous and leathery. Venation pattern: Palmate. Color: Young foliage, upper surface: Much darker than 147A; glossy. Young foliage, lower surface: Darker than 147B; glossy. Mature foliage, upper surface: Much darker than 147A; glossy. Mature foliage, lower surface: Close to 147A; glossy. Venation, upper surface: Much darker than 147A. Venation, lower surface: 146A to 147A. Petiole: Length: About 2.6 cm. Diameter: About 3 mm. Texture: Upper surface: Slightly pubescent. Lower surface: Smooth and glabrous. Color: 146A overlain with dark brown, 187A to 202A.

Flower description:

*Flower arrangement.*—Flowers arranged singly at terminal leaf axils. Very freely flowering with usually about three or four flower buds and/or open flowers per terminal apex. Flowers face upright or slightly outward.

*Flower appearance.*—Rounded, white-colored petals with pink throat. Flowers are open for about one day. Flowers persistent.

*Natural flowering season.*—Usually spring and summer or during periods of warm weather.

*Flower diameter.*—About 10.5 cm.

*Flower length* (*height*).—About 5.5 cm.

*Flower bud* (*just before showing color*).—Resistance to abscission during shipping: Plants of the new Hibiscus have been observed to resist flower bud drop when stored in a closed box for 5 days at 13° C. Rate of opening: About one or two days depending on temperatures. Length: About 2.3 cm. Diameter: About 1 cm. Shape: Oblong. Color: Close to 147A.

*Petals.*—Arrangement: Corolla consists of five petals that are fused at base; overlapping towards apex. Length: About 7.1 cm. Width: At widest point, about 6 cm; at base, about 1.3 cm. Shape: Roughly spatulate. Apex: Rounded. Base: Attenuate. Margin: Entire. Texture: Upper surface: Smooth, glabrous, satiny. Lower surface: Glabrous; somewhat rugose. Color: When opening and fully opened, upper surface: White, 155D. When opening and fully opened, lower surface: White, 155D. Throat: Pink, close to 52B to 52C; glossy.

*Sepals.*—Appearance: Five sepals fused into a tubular star-shaped calyx. Length: About 3 cm. Width: About 1 cm. Shape: Narrowly oblong. Apex: Sharply acute. Margin: Entire. Texture: Inner (upper) surface: Smooth, glabrous, waxy. Outer (lower) surface: Leathery, rough; pubescent at margins. Color: Inner (upper) surface: Close to 144A; glossy. Outer (lower) surface: Much darker than 146A.

*Bracts.*—Appearance: About six or seven fused at base. Length: About 1.9 cm. Width: About 4 mm. Shape: Linear. Apex: Acute. Margin: Entire. Texture, upper and lower surfaces: Smooth, glabrous, waxy. Color, upper and lower surfaces: 147A.

*Peduncles.*—Length: Short, about 2.2 cm. Diameter: About 2.5 mm. Angle: Upright to slightly bent. Strength: Strong, flexible. Texture: Smooth, glabrous. Color: Close to 146A.

*Reproductive organs.*—Androecium: Stamen number: Numerous, about 68. Filament length: About 6.5 mm. Filament color: 155D. Anther shape: Globular. Anther size: About 1 mm by 1 mm. Anther color: Close to 45A. Amount of pollen: Abundant. Pollen color: Close to 14A. Gynoecium: Pistil length: About 6.4 cm. Pistil diameter: Apex: About 2.5 mm. Base: About 7.5 mm. Style texture: Smooth, waxy. Style color: Towards base, 52B; mid-section, 52C; towards apex, 52D. Stigma appearance: Five, rounded. Stigma diameter: About 3 mm. Stigma color: 45A. Ovary color: 154C to 154D.

*Seed.*—Seed production has not been observed.

Disease resistance: Plants of the new Hibiscus grown under Florida production conditions have shown to be relatively resistant to pathogens common to Hibiscus.

It is claimed:

1. A new and distinct Hibiscus plant named 'Cool Wind', as illustrated and described.

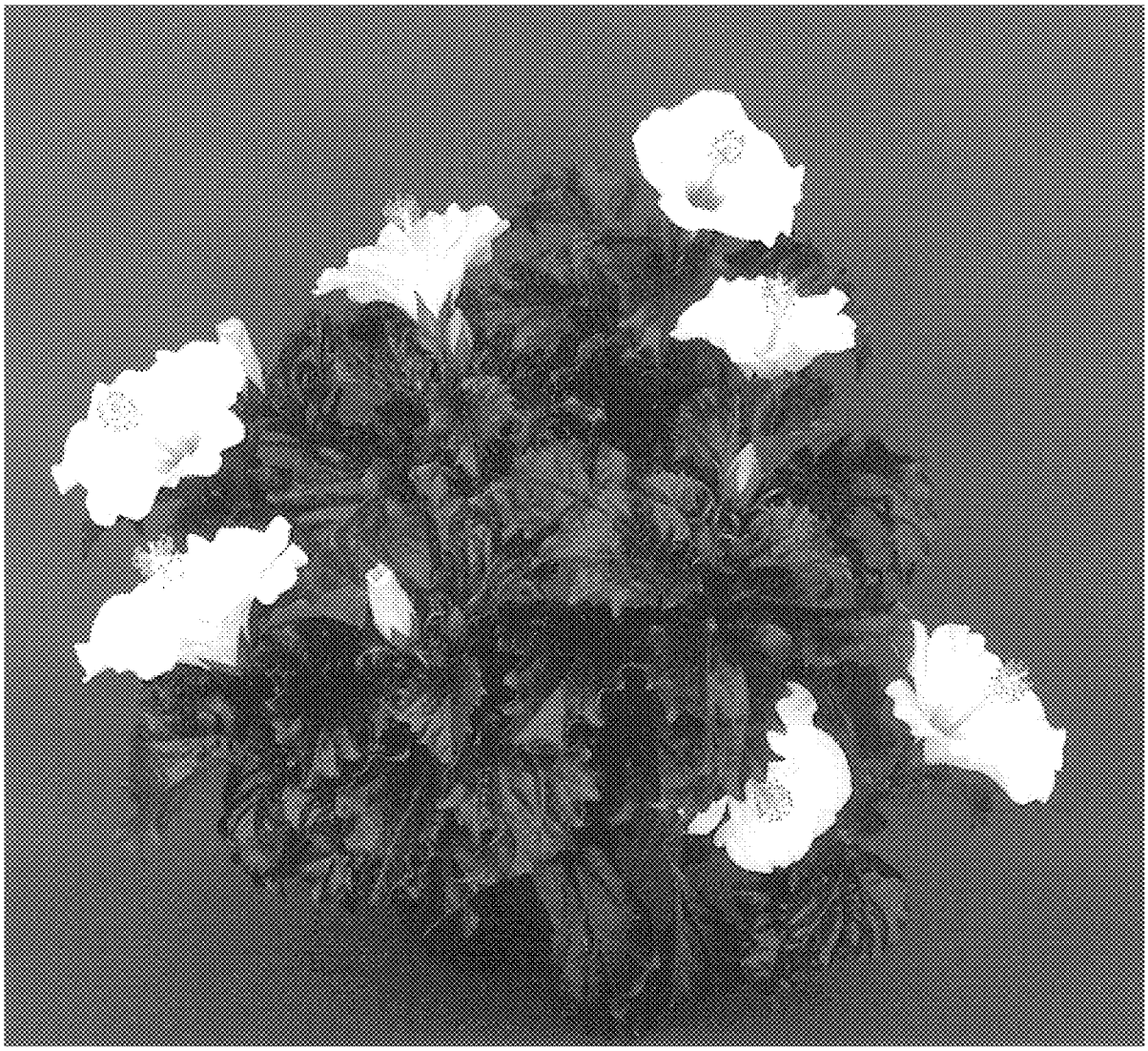

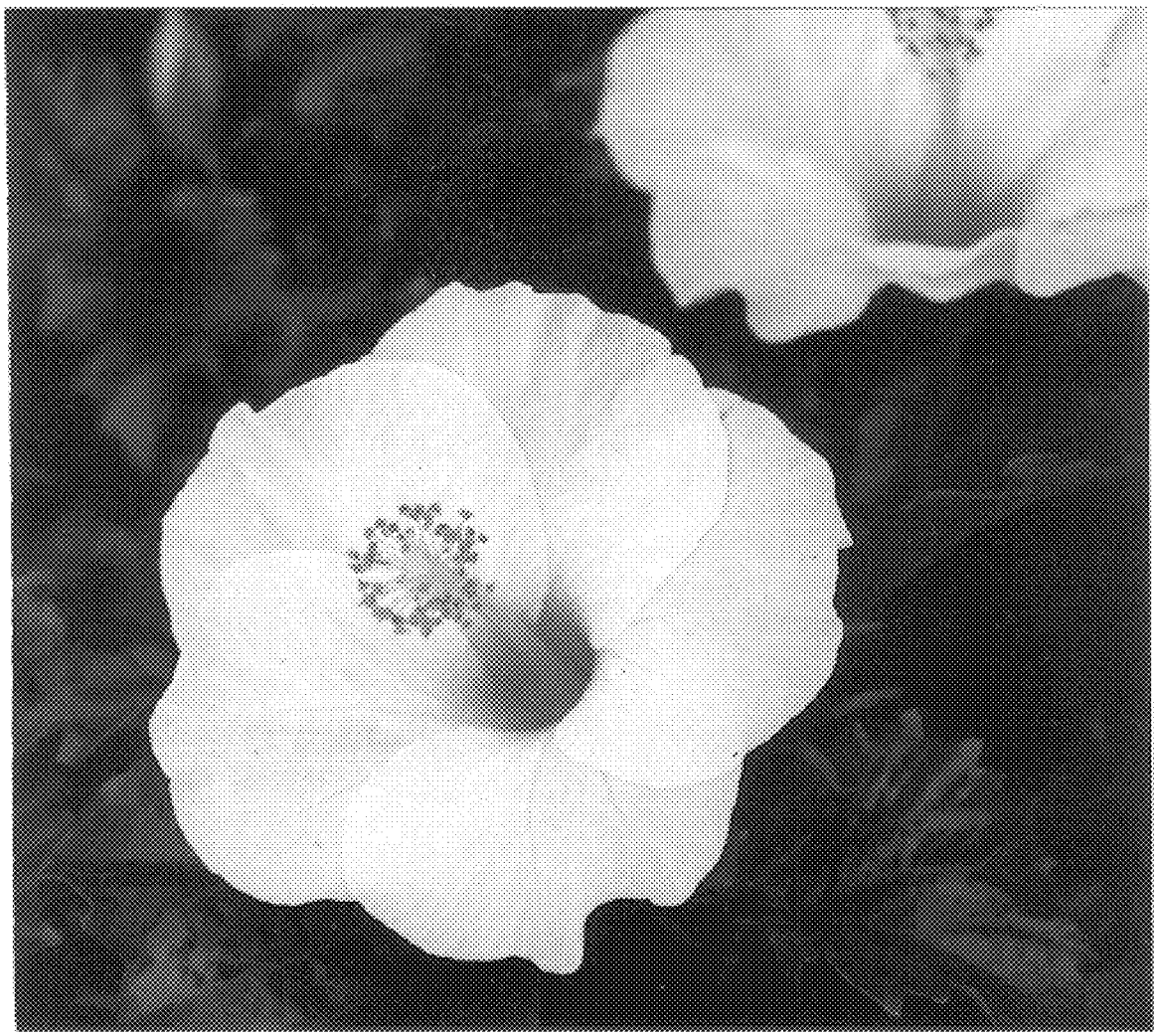

* * * * *